US009463144B2

(12) United States Patent
Shukla et al.

(10) Patent No.: US 9,463,144 B2

(45) Date of Patent: Oct. 11, 2016

(54) ADHESIVE COMPOSITION SUITABLE FOR DENTAL USES

(76) Inventors: Brian A. Shukla, Woodbury, MN (US); Bradley D. Craig, Lake Elmo, MN (US)

( * ) Notice: Subject to any disclaimer, the term of this patent is extended or adjusted under 35 U.S.C. 154(b) by 0 days.

(21) Appl. No.: 13/879,682

(22) PCT Filed: Nov. 3, 2011

(86) PCT No.: PCT/US2011/059046

§ 371 (c)(1), (2), (4) Date: Apr. 16, 2013

(87) PCT Pub. No.: WO2012/064573

PCT Pub. Date: May 18, 2012

(65) Prior Publication Data

US 2013/0224692 A1 Aug. 29, 2013

Related U.S. Application Data

(60) Provisional application No. 61/411,956, filed on Nov. 10, 2010.

(51) Int. Cl.

| | |
|---|---|
| ***C08F 2/46*** | (2006.01) |
| ***C08G 61/04*** | (2006.01) |
| ***A61K 6/00*** | (2006.01) |
| ***A61K 6/02*** | (2006.01) |
| ***A61K 6/083*** | (2006.01) |
| ***A61C 5/00*** | (2006.01) |
| ***A61C 7/16*** | (2006.01) |
| ***A61C 13/15*** | (2006.01) |

(52) U.S. Cl.

CPC ............... *A61K 6/0023* (2013.01); *A61C 5/00* (2013.01); *A61C 7/16* (2013.01); *A61C 19/003* (2013.01); *A61K 6/0008* (2013.01); *A61K 6/0029* (2013.01); *A61K 6/024* (2013.01); *A61K 6/083* (2013.01)

(58) Field of Classification Search

CPC .. A61K 6/0023; A61K 6/024; A61K 6/0029; A61K 6/083; A61K 6/0008; A61C 5/00; A61C 19/003; A61C 7/16; C08L 33/00; C08L 33/06; C08L 33/16

USPC .................................................. 522/1; 520/1

See application file for complete search history.

(56) References Cited

U.S. PATENT DOCUMENTS

| | | | | |
|---|---|---|---|---|
| 4,642,126 | A | 2/1987 | Zador | |
| 4,652,274 | A | 3/1987 | Boettcher | |
| 5,130,347 | A * | 7/1992 | Mitra | 522/149 |
| 5,530,038 | A | 6/1996 | Yamamoto | |
| 6,387,981 | B1 | 5/2002 | Zhang | |
| 6,566,413 | B1 | 5/2003 | Weinmann | |
| 6,624,236 | B1 | 9/2003 | Bissinger | |
| 6,852,795 | B2 | 2/2005 | Bissinger | |
| 6,852,822 | B1 | 2/2005 | Bissigner | |
| 6,916,858 | B2 | 7/2005 | Kojima | |
| 7,449,499 | B2 | 11/2008 | Craig | |
| 7,632,098 | B2 * | 12/2009 | Falsafi et al. | 433/215 |
| 7,649,029 | B2 | 1/2010 | Kolb | |
| 2005/0009946 | A1 | 1/2005 | Oguri | |
| 2005/0252413 | A1 * | 11/2005 | Kangas et al. | 106/35 |
| 2005/0252414 | A1 | 11/2005 | Craig | |
| 2005/0256223 | A1 | 11/2005 | Kolb | |
| 2006/0130701 | A1 | 6/2006 | Salz | |
| 2007/0254998 | A1 | 11/2007 | Orlowski | |
| 2009/0035728 | A1 | 2/2009 | Aasen | |
| 2010/0285419 | A1 | 11/2010 | Cinader, Jr. | |

FOREIGN PATENT DOCUMENTS

| | | |
|---|---|---|
| CA | 2254649 | 11/1998 |
| DE | 10 2006 045 628 | 4/2008 |
| JP | 2002-087917 | 3/2002 |
| WO | 2005/117805 | 12/2005 |
| WO | 2005/117806 | 12/2005 |
| WO | 2005/117807 | 12/2005 |
| WO | 2007/079144 | 7/2007 |
| WO | 2007/079166 | 7/2007 |
| WO | 2010/093534 | 8/2010 |
| WO | 2011/056450 | 5/2011 |
| WO | 2011/056452 | 5/2011 |

OTHER PUBLICATIONS

International Search Report PCT/US2011/059046 Oct. 18, 2012, 4 pgs.

* cited by examiner

*Primary Examiner* — Ling Choi

*Assistant Examiner* — Jessica E Whiteley

(57) ABSTRACT

A dental adhesive composition is described comprising a photocurable ionomer, radiopaque metal oxide nanoparticles, a phosphorous-containing acidic monomer, other polymerizable resin components, and a polar solvent. In a favored embodiment, the adhesive composition comprises a photocurable ionomer in an amount up to 15 wt-%; 5 wt-% to 30 wt-% of radiopaque metal oxide nanoparticles that comprise a basic surface (such as zirconia) wherein the nanoparticles comprise an organosilane surface treatment; a phosphorous-containing acidic monomer in an amount up to 10 wt-%; and 10 wt-% to 50 wt-% of solvent comprising water and at least one alcohol, ketone, or mixture thereof.

15 Claims, No Drawings

ADHESIVE COMPOSITION SUITABLE FOR DENTAL USES

BACKGROUND

Various dental adhesive compositions and dental cements, that comprise a water dispersible polymeric film former, have been described.

Self-etching dental compositions, such as those described in U.S. Pat. No. 6,916,858 and U.S. Pat. No. 7,449,499, have also been described.

Radiopacity is a desired feature in restorative dental materials because it allows visualization on x-ray films. A radiopaque two-part self-etching dental adhesive composition has been commercially available from 3M since 2007. Radiopacity was imparted to the adhesive composition by the inclusion of zirconia nanoparticles comprising a carboxylic acid surface treatment.

It is also desirable to include photocurable ionomers, such as described U.S. Pat. No. 5,130,347, in a dental adhesive composition to improve dentin adhesion.

SUMMARY

It has been found that the carboxylic acid groups of the photocurable ionomer react with the carboxylic acid groups of the surface treated zirconia nanoparticles causing gellation in short timeframes.

Industry would find advantage in overcoming such gelation, thereby providing radiopaque adhesive compositions having improved dentin adhesion In one embodiment, a dental adhesive composition is described comprising a photocurable ionomer, radiopaque metal oxide nanoparticles, a phosphorous-containing acidic monomer, other polymerizable resin components, and a polar solvent. In a favored embodiment, the adhesive composition comprises a photocurable ionomer in an amount up to 15 wt-%; 5 wt-% to 30 wt-% of radiopaque metal oxide nanoparticles that comprise a basic surface (such as zirconia) wherein the nanoparticles comprise an organosilane surface treatment; a phosphorous-containing acidic monomer in an amount up to 10 wt-%; and 10 wt-% to 50 wt-% of solvent comprising water and at least one alcohol, ketone, or mixture thereof.

The adhesive composition can advantageously be provided as a one-part dispersion wherein all the components have been premixed in a single container. Further, such adhesive composition is stable a 45° C. for at least 90 days.

In other embodiments, methods of applying a dental composition are described comprising providing a dental adhesive as described herein; applying the dental adhesive to a hard tissue surface; and hardening the dental composition by photocuring. The method typically further comprises contacting the dental adhesive with a curable dental restoration material or preformed dental article prior to hardening.

DETAILED DESCRIPTION

As used herein, "adhesive" or "dental adhesive" refers to a composition used as a pre-treatment on a dental structure (e.g., a tooth) to adhere a "dental material" (e.g., "restorative,") or a dental article such as an orthodontic appliance (e.g., bracket)) to a dental structure. Since a primer is also a pre-treatment, as used herein the term "adhesive" also includes primers to the extent such primers include an adhesion promoting polymer additive and a polymerizable component as described herein.

As used herein, "dental material" refers to a material that may be bonded to a dental structure surface and includes, for example, dental restoratives.

Dental restoration materials and dental cements typically comprises an inorganic oxide filler content substantially greater than a dental adhesive. Whereas the dental adhesive described herein comprises up to 30 wt-% filler, dental cements generally comprise at least 50 wt-% filler. Further, dental restoration materials generally comprise greater than 60 wt-%, and more preferably greater than 70 wt-% of nanoscopic inorganic filler.

Preferred dental articles include a preformed crown, a preformed inlay, a preformed onlay, a preformed bridge, a preformed veneer, a preformed orthodontic appliance, a preformed maxillofacial prosthesis, a preformed tooth facsimile, or a preformed tooth splint. Preformed articles for dental implants include healing caps as well as articles having tooth-shaped supragingival surfaces as described in WO2010/093534. Further, such articles may comprise an embedded implant abutment, such as described in WO2011/056452 and WO2011/056450.

In some embodiments, the dental structure surface can be pre-treated, e.g., by etching, priming, and/or applying an adhesive to enhance the adhesion with the dental material.

As used herein, an "etchant" refers to an acidic composition that is capable of fully or partially solubilizing (i.e., etching) a dental structure surface. The etching effect can be visible to the naked human eye and/or instrumentally detectable (e.g., by light microscopy). Typically, an etchant is applied to the dental structure surface for a period of about 10 to 30 seconds.

As used herein, a "self-etching" composition refers to a composition that bonds to a dental structure surface without pretreating the dental structure surface with an etchant. Preferably, a self-etching composition can also function as a self-primer wherein no primer is used.

As used herein, "hardening" or "curing" a composition are used interchangeably and refer to polymerization and/or crosslinking reactions including, for example, photo polymerization reactions and chemical polymerization techniques (e.g., ionic reactions or chemical reactions forming radicals effective to polymerize ethylenically unsaturated compounds) involving one or more materials included in the composition.

As used herein, "(meth)acryl" is a shorthand term referring to "acryl" and/or "methacryl." For example, a "(meth)acryloxy" group is a shorthand term referring to either an acryloxy group (i.e., $CH_2{=}CHC(O)O-$) and/or a methacryloxy group (i.e., $CH_2{=}C(CH_3)C(O)O-$).

As used herein, a "hard tissue surface" refers to tooth structures (e.g., enamel, dentin, and cementum) and bone.

Presently described are adhesive compositions and methods of bonding (e.g. hard) to dental tissue. The adhesive will be described herein with respect to dental uses and thus will be referred to herein as a "dental adhesive". However, the adhesive can be used for other uses such as the bonding of ceramic materials.

The dental adhesive described herein comprises a hardenable resin. The compositions are typically photopolymerizable, i.e., the compositions contain a photoinitiator (i.e., a photoinitiator system) that upon irradiation with actinic radiation initiates the polymerization (or hardening) of the composition. Such photopolymerizable compositions can be free-radically polymerizable.

The dental adhesive compositions described herein comprise a photocurable ionomer, i.e. a polymer having pendent ionic groups capable of a setting reaction and pendent free radically polymerizable groups to enable the resulting mixture to be polymerized, i.e., cured, upon exposure to radiant energy.

As described for example in U.S. Pat. No. 5,130,347, photocurable ionomers have the general formula:

$$B(X)_m(Y)_n$$

wherein

B represents an organic backbone, each X independently is an ionic group, each Y independently is a photocurable group, m is a number having an average value of 2 or more, and n is a number having an average value of 1 or more.

Preferably the backbone B is an oligomeric or polymeric backbone of carbon-carbon bonds, optionally containing non-interfering substituents such as oxygen, nitrogen or sulfur heteroatoms. The term "non-interfering" as used herein refers to substituents or linking groups that do not unduly interfere with either the photocuring reaction of the photocurable ionomer.

Preferred X groups are acidic groups, with carboxyl groups being particularly preferred.

Suitable Y groups include, but are not limited to, polymerizable ethylenically unsaturated groups and polymerizable epoxy groups. Ethylenically unsaturated groups are preferred, especially those that can be polymerized by means of a free radical mechanism, examples of which are substituted and unsubstituted acrylates, methacrylates, alkenes and acrylamides.

X and Y groups can be linked to the backbone B directly or by means of any non-interfering organic linking group, such as substituted or unsubstituted alkyl, alkoxyalkyl, aryl, aryloxyalkyl, alkoxyaryl, aralkyl, or alkaryl groups.

Preferred photocurable ionomers are those in which each X is a carboxyl group and each Y is an ethylenically unsaturated group such as a (meth)acrylate group that can be polymerized by a free radical mechanism. Such ionomers are conveniently prepared by reacting a polyalkenoic acid (e.g., a polymer of formula $B(X)_{m+n}$ wherein each X is a carboxyl group) with a coupling compound containing both an ethylenically unsaturated group and a group capable of reacting with a carboxylic acid group such as an NCO group. The resulting photocurable ionomer preferably has least one of the free radically polymerizable (e.g. (meth)acrylate group)) is linked to said ionomer by means of an amide linkage. The molecular weight of the resultant photocurable ionomers is typically between about 1000 and about 100,000 g/mole.

The concentration of the photocurable ionomer is typically at least 0.5 wt-%, 1 wt-%, or 1.5 wt-% and typically no greater than 15 wt-%. In some embodiments, the concentration of photocurable ionomer is no greater than 14 wt-%, 13 wt-% or 12 wt-%.

The dental adhesive compositions described herein comprise one or more hardenable components in the form of ethylenically unsaturated compounds with acid and/or acid-precursor functionality in addition to the photocurable ionomer that typically comprises carboxyl groups. Acid-precursor functionalities include, for example, anhydrides, acid halides, and pyrophosphates. The acid functionality can include phosphoric acid functionality, phosphonic acid functionality, sulfonic acid functionality, or combinations thereof. Typically, the adhesive compositions described herein comprise little (e.g. less than 10 wt-%, 5 wt-%, or 1 wt-%) or no ethylenically unsaturated compounds with carboxylic acid functionality when the radiopaque filler comprises a basic surface, such as in the case of zirconia.

Ethylenically unsaturated compounds with acid functionality include, for example, alpha, beta-unsaturated acidic compounds such as glycerol phosphate mono(meth)acrylates, glycerol phosphate di(meth)acrylates, hydroxyethyl (meth)acrylate phosphates (e.g. HEMA-P), bis((meth)acryloxyethyl) phosphate, ((meth)acryloxypropyl) phosphate, bis((meth)acryloxypropyl) phosphate, bis((meth)acryloxy) propyloxy phosphate, (meth)acryloxyhexyl phosphate, bis ((meth)acryloxyhexyl) phosphate (e.g. MHP), (meth)acryloxyoctyl phosphate, bis((meth)acryloxyoctyl) phosphate, (meth)acryloxydecyl phosphate, bis((meth)acryloxydecyl) phosphate, and caprolactone methacrylate phosphate.

In some embodiments, the adhesive composition comprises at least 0.5 wt-%, 1 wt-%, or 2 wt-% and typically no greater than 10 wt-% of ethylenically unsaturated compounds with acid functionality, based on the total weight of the composition. In some embodiments, the concentration ethylenically unsaturated compounds with acid functionality is no greater than 9 wt-%, 8 wt-%, 7 wt-%, 6 wt-% or 5 wt-%. Phosphorus-containing acid monomers having at least one P—OH moiety, such as 6-methacryloxyhexyl phosphate, are typically preferred. Self-etching adhesive compositions typically comprise ethylenically unsaturated compounds with acid functionality at a concentration of at least 50 wt-%, 60 wt-% or 70 wt-%.

The dental adhesive composition typically further comprises other polymerizable resin components, i.e. in addition to the photocurable ionomer and ethylenically unsaturated compound(s) with acid and/or acid-precursor functionality. The adhesive composition generally comprises such other free-radically components at a concentration of at least 30 wt-% or 35 wt-% and no greater than 50 wt-% or 55 wt-% in addition to the photocurable ionomer and phosphorous-containing acidic monomer, as previously described.

Suitable photopolymerizable components of the dental adhesive composition described herein include, for example, epoxy resins (which contain cationically active epoxy groups), vinyl ether resins (which contain cationically active vinyl ether groups), ethylenically unsaturated compounds (which contain free radically active unsaturated groups, e.g., acrylates and methacrylates), and combinations thereof. Examples of useful ethylenically unsaturated compounds include acrylic acid esters, methacrylic acid esters, hydroxy-functional acrylic acid esters, hydroxy-functional methacrylic acid esters, and combinations thereof.

The polymerizable resin of the adhesive composition typically includes one or more hardenable components in the form of ethylenically unsaturated compounds without acid functionality.

Suitable compounds contain at least one ethylenically unsaturated bond and are capable of undergoing (e.g. free-radical) addition polymerization. Such free radically polymerizable compounds include mono-, di- or poly-(meth)acrylates (i.e., acrylates and methacrylates) such as, methyl (meth)acrylate, ethyl acrylate, isopropyl methacrylate, n-hexyl acrylate, stearyl acrylate, allyl acrylate, glycerol triacrylate, ethyleneglycol diacrylate, diethyleneglycol diacrylate, triethyleneglycol dimethacrylate (TEGDMA), 1,3-propanediol di(meth)acrylate, trimethylolpropane triacrylate, 1,2,4-butanetriol trimethacrylate, 1,4-cyclohexanediol diacrylate, pentaerythritol tetra(meth)acrylate, sorbitol hexacrylate, tetrahydrofurfuryl (meth)acrylate, bis[1-(2-acryloxy)]-p-ethoxyphenyldimethylmethane, bis[1-(3-acryloxy-2-hydroxy)]p-propoxyphenyldimethylmethane, ethoxylated bisphenolA di(meth)acrylate, and trishydroxyethyl-isocyanurate trimethacrylate; (meth)acrylamides (i.e., acrylamides and methacrylamides) such as (meth)acrylamide, methylene bis-(meth)acrylamide, and diacetone (meth) acrylamide; urethane (meth)acrylates; the bis-(meth)acrylates of polyethylene glycols (preferably of molecular weight 200-500), copolymerizable mixtures of acrylated monomers such as those in U.S. Pat. No. 4,652,274 (Boettcher et al.), acrylated oligomers such as those of U.S. Pat. No. 4,642,126 (Zador et al.). Other suitable free radically polymerizable compounds include siloxane-functional (meth)acrylates as disclosed, for example, in WO-00/38619 (Guggenberger et al.), WO-01/92271 (Weinmann et al.), WO-01/07444 (Guggenberger et al.), WO-00/42092 (Guggenberger et al.). Mixtures of two or more free radically polymerizable compounds can be used if desired.

The adhesive composition preferably comprises a hardenable component comprising a hydroxyl group(s) and ethylenically unsaturated group(s) in a single molecule. Examples of such materials include hydroxyalkyl (meth) acrylates, such as 2-hydroxyethyl (meth)acrylate (HEMA) and 2-hydroxypropyl (meth)acrylate; glycerol mono- or di-(meth)acrylate (e.g. GDMA); trimethylolpropane mono- or di-(meth)acrylate; pentaerythritol mono-, di-, and tri-(meth)acrylate; sorbitol mono-, di-, tri-, tetra-, or penta-(meth)acrylate, and 2,2-bis[4-(2-hydroxy-3-methacryloyloxy-propoxy)phenyl]propane (BisGMA). Suitable ethylenically unsaturated compounds are also available from a wide variety of commercial sources, such as Sigma-Aldrich, St. Louis, Mo. Mixtures of ethylenically unsaturated compounds can be used if desired.

In some embodiments, the other (e.g. free-radically) polymerizable components of the polymerizable resin may comprise about 30 to 50 wt-% of BisGMA, about 20 to 40 wt-% of HEMA, and about 15 to 35 wt-% of GDMA. Such polymerizable resin may further comprise up to about 15 wt-% of a diurethane diacrylate (UDMA).

The (e.g. cured) dental adhesive compositions described herein further comprise radiopaque metal oxide nanoparticles. By radiopaque it is meant that the (e.g. cured) adhesive composition does not permit the passage of x-rays. The radiopacity of the cured adhesive composition is typically at least equivalent to the radiopacity of aluminum at a thickness of 1.0 mm.

The radiopaque metal oxide nanoparticles have an average primary particle size of less than about 0.100 micrometers (i.e., microns), and more preferably less than 0.075 microns. The nanoscopic particulate filler comprises zirconia. The filler can have a unimodal or polymodal (e.g., bimodal) particle size distribution. The nanoscopic particulate material typically has an average primary particle size of at least about 2 nanometers (nm), and preferably at least about 7 nm. Preferably, the nanoscopic particulate material has an average primary particle size of no greater than about 50 nm, and more preferably no greater than about 20 nm in size. The average surface area of such a filler is preferably at least about 20 square meters per gram ($m^2/g$), more preferably, at least about 50 $m^2/g$, and most preferably, at least about 100 $m^2/g$.

The radiopaque metal oxide nanoparticles generally comprise a heavy metal or mixed metal oxide comprising a heavy metal. The atomic number of the heavy metal is typically at least 28 (nickel), 29 (copper), or 30 (zinc). For dental adhesives, biocompatibility of the radiopaque metal oxide nanoparticles is an important consideration. For dental uses, radiopaque metal oxide nanoparticles preferably comprise zirconia such as a mixed metal oxide comprising at least 50, 60, 70, 80, 90, or 95 mole % zirconia.

When the radiopaque metal oxide nanoparticles have a basic surface, such as in the case of zirconia, the nanoparticles are surface treated with an organometallic coupling agent, such as an organosilane. The organometallic coupling agent may be functionalized with reactive curing groups, such as acrylates, methacrylates, vinyl groups and the like. Suitable copolymerizable organometallic compounds include organosilanes having the general formulas: $CH_2{=}C(CH_3)_mSi(OR)_n$ or $CH_2{=}C(CH_3)_mC{=}OOASi(OR)_n$; wherein m is 0 or 1, R is an alkyl group having 1 to 4 carbon atoms, A is a divalent organic linking group, and n is from 1 to 3. Such silane compounds typically have a molecular weight of less than 350 g/mole or less than 300 g/mole. Preferred coupling agents include gamma-methacryloxypropyltrimethoxysilane (GF-31 available from Geniosil GF-31), gamma-mercaptopropyltriethoxysilane, gamma-aminopropyltrimethoxysilane, and the like.

The dental adhesive described herein comprises radiopaque metal oxide nanoparticles, such as surface treated zirconia nanoparticles, in an amount of at least 5 wt-%, 6 wt-%, 7 wt-%, 8 wt-%, 9 wt-%, or 10 wt-% based on the total weight of the composition. The total concentration of surface treated zirconia nanoparticles is typically no greater than 30 wt-%, based on the total weight of the composition. In some embodiments, the dental adhesive composition comprises no greater than 25 wt-%, 24 wt-%, 23 wt-%, 22 wt-%, 21 wt-% or 20 wt-%.

The adhesive composition may optionally comprise low concentrations of other fillers, provided the presence thereof does not detract from the radiopacity contributed by the radiopaque metal oxide nanoparticles (e.g. surface treated zirconia nanoparticles). The adhesive composition is typically free of acid-reactive filler such untreated metal oxides and acid-reactive glasses such as fluoroaluminosilicate (FAS) glass.

In favored embodiments, the adhesive composition is an aqueous dental adhesive comprising the photocurable ionomer, radiopaque metal oxide nanoparticles, phosphorous-containing acidic monomer, and other polymerizable resin components dispersed in a polar solvent. The polar solvent typically comprises water and a cosolvent such as an alcohol (e.g. ethanol or isopropyl alcohol) or ketone (e.g. acetone, and mixtures thereof). The concentration of organic solvent is typically at least 10 wt-% or 15 wt-% or 20 wt-%. Further, the concentration of solvent is no greater than 50 wt-%. The adhesive composition typically comprises an appreciable amount of solvent relative to the concentration of radiopaque metal oxide nanoparticles. In some embodiments, the ratio of solvent to filler is typically at least 1 to 2, or 1 to 1.5 or 1:1.

The other polymerizable resin components can also serve as a diluent for the radiopaque metal oxide nanoparticles, provided that such component has a sufficiently low molecular weight. Hence, the solvent concentration may be lower than the ratios just described when the adhesive composition comprises sufficient concentration of such polymerizable diluents.

The viscosity, with units of centistokes (CTS), can be measured with a Cannon-Fenske #450 viscometer (Cannon Instrument Co., State College, Pa.) that equilibrated in a water bath maintained at 25° C. The viscometer is filled to just above mark "C" with adhesive, and the flow time of the adhesive from mark "C" to mark "E" on the viscometer was measured. Viscosity can be calculated as:

$$t*k$$

where t is the time (in seconds) for the meniscus of the adhesive to pass from mark "C" to mark "E", and k is the viscometer constant (units of CTS/s) specific to that viscometer.

The viscosity of the adhesive composition is typically at least 15 or 20 centistokes and no greater than 200 centistokes or 150 centistokes. In some embodiments, the viscosity is not greater than 100, 75, or 50 centistokes. The higher viscosity materials are suitable for bonding to enamel. However, the lower viscosity adhesive compositions are typically preferred for bonding to dentin. Further, the lower viscosity adhesive compositions may also be employed as a primer, used in combination with a dental cement, to bond articles. The adhesive composition in the invention may optionally contain polymerization inhibitors, antioxidants, UV absorbents, pigments dyes and other additives in addition to the ingredients noted above. A fluorine compound having anticarious capabilities, such as sodium fluoride, may be incorporated in the adhesive composition.

Methods of the present invention provide for the treatment of hard tissues, including human and animal tissues. Hard tissues include, for example, bone, teeth, and the component parts of teeth (e.g., enamel, dentin, and cementum). Specific methods of use are described in U.S. Pat. No. 7,448,499; incorporated herein by reference.

The dental adhesive described herein is preferably a one-part stable dispersion, wherein all the components have been premixed in a single container. Due to the combination of components as described herein, the composition advantageously forms a stable dispersion at 45° C. for at least 90 days (as determined as described in the examples). When the dental adhesive includes two or more parts, the two or more parts are preferably mixed just prior to or during the application process. Suitable mixing devices include, for example, static mixing devices.

The dental adhesive compositions are hardened, for example, by inducing the polymerizable organic components to react. For example, when the composition includes an ethylenically unsaturated group, polymerization may be induced by the application of actinic radiation. Preferably the composition is irradiated with radiation having a wavelength of 400 to 1200 nanometers, and more preferably with visible radiation.

Visible light sources include, for example, the sun, lasers, metal vapor (e.g., sodium and mercury) lamps, incandescent lamps, halogen lamps, mercury arc lamps, fluorescent room light, light emitting diodes, tungsten halogen lamps, and xenon flash lamps.

In some embodiments, the compositions are hardened (e.g., polymerized by conventional photo polymerization and/or chemical polymerization techniques) prior to applying the dental material. In other embodiments, the compositions are hardened (e.g., polymerized by conventional photo polymerization and/or chemical polymerization techniques) after applying the dental material. In some embodiments, the adhesive composition can promote adhesion to both enamel and dentin. Further, the composition may be formulated to function as the etchant, primer, and adhesive to both enamel and dentin.

Once the adhesive composition of the present invention has been hardened, the composition is generally not readily removed. Methods of bonding a dental material to a dental structure surface preferably result in a bond to enamel or dentin (or preferably both), of at least 10 MPa, more preferably at least 15, MPa, and most preferably at least 20 MPa when tested according to the Notched Edge Shear Adhesion test method described in the examples.

The present invention is illustrated by the following examples. It is to be understood that the particular examples, materials, amounts, and procedures are to be interpreted broadly in accordance with the scope and spirit of the invention as set forth herein. Unless otherwise indicated, all parts and percentages are on a weight basis, all water is deionized water, and all molecular weights are weight average molecular weight.

| Component | Source |
|---|---|
| BisGMA (Bisphenol A diglycidyl ether methacrylate) | Sigma-Aldrich, St. Louis, MO |
| HEMA (2-hydroxyethyl methacrylate) | Sigma-Aldrich |
| GDMA (glycerol dimethacrylate) | Rohm Tech Inc., Malden, MA |
| UDMA (diurethane dimethacrylate) | Dajac Laboratories, Trevose, PA |
| MHP (6-methacryloxyhexyl phosphate) | Prepared as described for MHP-B in Column 24 of U.S. Pat. No. 7,632,098 |
| HEMA-Phosphate (mixture of mono-, di-, tri-HEMA phosphate and tetraHEMA pyrophosphate) | Prepared as described for HEMA-P in Columns 24-25 of U.S. Pat. No. 7,632,098 |
| MDP (mixture including 10-methacryloyloxydecyl dihydrogen phosphate) | Prepared as described in [0137] of US 2009/0035728 |
| Water deionized | |
| Ethanol 200 proof | |
| Photocurable ionomer (VCP) | Prepared as described in Example 11 of U.S. Pat. No. 5,130,347 |
| Silane treated zirconia | Can be prepared as described in Preparatory Example 1A of US 2005/0252413, except for the substitution of GF-31 Silane (Wacker Chemie, Germany) for the blend of Silquest A-174 and A-1230 |
| MEEAA (2-(2-(2-methoxyethoxy)ethoxy) acetic acid) | Sigma-Aldrich |
| CPQ (camphorquinone) | Sigma-Aldrich |
| EDMAB (ethyl 4-(N,N-dimethylamino) benzoate) | Sigma-Aldrich |
| DPIHFP (diphenyl iodonium hexafluorophosphate) | Alpha Aesar, Ward Hill, MA |

Test methods: stability assessment and shear bond strength

Dispersion Stability Assessment:

After compounding, each adhesive was transferred into a clear plastic vial, capped, placed into a 45 deg. C. aging oven, and checked visually on a regular basis to assess the nanozirconia dispersion stability over time. A stable composition has a clear appearance, whereas an unstable composition is indicated by clouding, increasing turbidity, gelation or phase separation.

Shear Bond Strength:

Potted bovine teeth were ground using 120 grit sand paper to expose enamel or dentin, then teeth were further polished using 320 grit sand paper to smooth the surface. The bovine tooth surface was dried by applying a stream of compressed air for 3 seconds, then a drop of primer was applied, scrubbed for 20 seconds, dried by a stream of compressed air for 20 seconds, followed by application of a thin layer of adhesive (the adhesive composition is described below) with scrubbing for 20 seconds. The primer and adhesive combination was then cured for 20 seconds with a dental blue curing (3M ESPE Elipar Freelight 2) for 20 seconds. Previously prepared molds made from a 2.5-mm thick "Teflon" sheet with a 4.7 mm diameter hole through the sheet were clamped to each prepared tooth so that the central axis of the hole in the mold was normal to the tooth surface. The hole in each mold was filled with a visible light-curable dental restorative (available from 3M ESPE as "Filtek™ Z250 Restorative" A2 shade) and cured for 20 seconds irradiation with the dental curing light. The teeth and molds were allowed to stand for about 5 minutes at room temperature, then stored in distilled water at 37° C. for 24 hours unless otherwise noted. The molds were then carefully removed from the teeth, leaving a molded button of restorative attached to each tooth.

The adhesive strength was evaluated utilizing the wire loop method by mounting the acrylic disk in a holder clamped in the jaws of an "Instron 1123" apparatus with the polished tooth surface oriented parallel to the direction of pull. A loop of orthodontic wire (0.44 mm diameter) was placed around the restorative button adjacent to the polished tooth surface. The ends of the orthodontic wire were clamped in the pulling jaw of the Instron apparatus, thereby placing the bond in shear stress. The bond was stressed until it (or the dentin or button) failed using a crosshead speed of 2 mm/min. Five adhesion samples were prepared for each set of primer and adhesive.

Preparatory Example: Resin Mixture

The resin mixture listed in Table 2 was formed by combining BisGMA (39 wt %), HEMA (29.85 wt %), GDMA (22.89 wt %), and UDMA (7.46 wt %) and mixing until uniform.

TABLE 2

Components

The components listed in Table 2 were mixed with a speed mixer by first combining the treated zirconia and the resin mixture, then adding the acidic monomers, photocurable ionomer, initiators, and solvents to form a uniform mixture.

Results

| Example Number | Resin Mixture | Silane Treated $ZrO_2$ | DI Water | Ethanol (200 proof) | VCP | MHP | MEEAA | 45 deg. C. Aging Results |
|---|---|---|---|---|---|---|---|---|
| CE 1 | 43.72 | 13.88 | 4.35 | 30.45 | 7.61 | | | dispersion failed within two days (sample gelled) |
| CE 2 | 47.32 | 15.02 | 4.71 | 32.96 | | | | stable dispersion at 115 days |
| Ex 1 | 42.84 | 13.6 | 4.26 | 29.84 | 7.61 | 1.85 | | stable dispersion at 112 days |
| Ex 2 | 41.97 | 13.32 | 4.18 | 29.23 | 7.61 | 3.7 | | stable dispersion at 112 days |
| CE 3 | 46.37 | 14.72 | 4.61 | 32.3 | | 2 | | stable dispersion at 112 days |
| CE 4 | 45.42 | 14.42 | 4.52 | 31.64 | | 4 | | stable dispersion at 112 days |
| CE 5 | 43.2 | 13.71 | 4.3 | 30.09 | 7.62 | | 1.09 | dispersion began failing within two days (opacified and thickened |
| CE 6 | 42.69 | 13.55 | 4.25 | 29.73 | 7.61 | | 2.18 | dispersion began failing within two days (opacified and thickened |

| Example Number | Resin Mixture | Silane Treated $ZrO_2$ | DI Water | Ethanol (200 proof) | VCP | MHP | HEMA-Phosphate | MDP | 45° C. Aging Results |
|---|---|---|---|---|---|---|---|---|---|
| Ex 3 | 43.04 | 13.67 | 4.35 | 30.45 | 7.61 | | 0.87 | | stable dispersion at 109 days |
| Ex 4 | 42.38 | 13.46 | 4.35 | 30.45 | 7.61 | | 1.75 | | stable dispersion at 109 days |

TABLE 2-continued

Components
The components listed in Table 2 were mixed with a speed mixer by first combining the treated zirconia and the resin mixture, then adding the acidic monomers, photocurable ionomer, initiators, and solvents to form a uniform mixture.
Results

| | | | | | | | | |
|---|---|---|---|---|---|---|---|---|
| Ex 5 | 42.83 | 13.61 | 4.35 | 30.45 | 7.61 | 1.15 | | stable dispersion at 109 days |
| Ex 6 | 41.96 | 13.33 | 4.35 | 30.45 | 7.61 | 2.3 | | stable dispersion at 109 days |
| Ex 7 | 42.62 | 13.54 | 4.35 | 30.45 | 7.61 | | 1.43 | stable dispersion at 109 days |
| Ex 8 | 41.54 | 13.2 | 4.35 | 30.45 | 7.61 | | 2.86 | stable dispersion at 109 days |

| Example Number | Resin Mixture | Silane Treated $ZrO_2$ | DI Water | Ethanol (200 proof) | VCP | MHP |
|---|---|---|---|---|---|---|
| Ex 9 | 41.06 | 13.75 | 4.31 | 30.18 | 7.55 | 2.28 |
| CE 7 | 46.48 | 15.57 | 4.31 | 30.19 | | 2.59 |
| Ex 10 | 45.13 | 15.12 | 4.31 | 30.19 | 1.89 | 2.51 |
| Ex 11 | 43.77 | 14.66 | 4.31 | 30.19 | 3.78 | 2.44 |
| Ex 12 | 42.42 | 14.21 | 4.31 | 30.18 | 5.66 | 2.36 |

| Example Number | CPQ | EDMAB | DPIHFP | Enamel Adhesion, MPa | Dentin Adhesion, MPa |
|---|---|---|---|---|---|
| Ex 9 | 0.302 | 0.216 | 0.345 | 32.9 (6.2) | 31.6 (8.0) |
| CE 7 | 0.302 | 0.216 | 0.345 | 29.2 (12.9) | 16.4 (8.1) |
| Ex 10 | 0.302 | 0.216 | 0.345 | 31.5 (13.6) | 26.9 (11.2) |
| Ex 11 | 0.302 | 0.216 | 0.345 | 31.3 (7.9) | 29.1 (4.1) |
| Ex 12 | 0.302 | 0.216 | 0.345 | 40.2 (6.4) | 29.2 (6.6) |

What is claimed is:

1. An adhesive composition comprising:

a one-part dispersion comprising the following components pre-mixed in a single container;

a photocurable ionomer having a molecular weight between 1000 and 100,000 g/mol in an amount up to 15 wt-% wherein the photocurable ionomer has the general formula:

$$B(X)_m(Y)_n$$

wherein

B represents an organic polymeric backbone, each X independently is an ionic group, each Y independently is a photocurable group, m is a number having an average value of 2 or more, and n is a number having an average value of 1 or more;

5 wt-% to 30 wt-% of radiopaque metal oxide nanoparticles;

phosphorous-containing acidic monomer(s);

30 wt-% to 50 wt-% of other polymerizable resin components; and 10 wt-% to 50 wt-% of solvent comprising water wherein the adhesive composition is substantially free of acid-reactive filler such that the adhesive composition is stable at 45° C. for at least 90 days.

2. The adhesive composition of claim 1 wherein the radiopaque metal oxide nanoparticles comprise an organosilane surface treatment.

3. The adhesive composition of claim 1 wherein the radiopaque metal oxide nanoparticles comprise zirconia.

4. The adhesive composition of claim 3 wherein the organosilane surface treatment is copolymerizable with the photocurable ionomer.

5. The adhesive composition of claim 1 wherein the photocurable ionomer comprises pendent ionic groups and pendent free-radically polymerizable groups and at least one of the polymerizable groups is linked to the ionomer by means of an amide linkage.

6. The adhesive composition of claim 1 wherein the photocurable ionomer comprises carboxyl groups and (meth)acrylate groups.

7. The adhesive composition of claim 1 wherein the radiopaque metal oxide nanoparticles are present in an amount of 10 wt-% to 30 wt-%.

8. The adhesive composition of claim 1 wherein the phosphorous-containing acidic monomer(s) is present in the adhesive composition in an amount up to 10 wt-%.

9. The adhesive composition of claim 1 wherein the adhesive is suitable for use as a dental adhesive.

10. A method of applying a dental composition comprising:

providing a dental adhesive of claim 1;

applying the dental adhesive to a hard tissue surface; and hardening the dental composition by curing.

11. The method of claim 10 wherein the hard dental tissue is selected from enamel, dentin, and a combination thereof.

12. The method of claim 10 wherein the adhesive is applied to the hard tissue surface with pretreating the surface with an etchant, primer, or combination thereof.

13. The method of claim 10 wherein the method further comprises contacting the dental adhesive with a curable dental restoration material or preformed dental article prior to hardening.

14. The method of claim 1 wherein the dental composition is hardened by photocuring.

15. The adhesive composition of claim 1 wherein the adhesive comprises at least 10 wt-% of polar solvent selected from alcohol, ketone, or mixture thereof.

* * * * *

UNITED STATES PATENT AND TRADEMARK OFFICE
CERTIFICATE OF CORRECTION

PATENT NO. : 9,463,144 B2
APPLICATION NO. : 13/879682
DATED : October 11, 2016
INVENTOR(S) : Brian Shukla et al.

It is certified that error appears in the above-identified patent and that said Letters Patent is hereby corrected as shown below:

In the Specification

Column 1
Line 32, after "adhesion" insert -- . --.
Line 49, delete "a" and insert -- at --, therefor.

Column 4
Line 65, delete "hexacrylate," and insert -- hexaacrylate, --, therefor.
Line 67, delete "p-" and insert -- -p- --, therefor.

Column 8
Line 47 (approx.), delete "Alpha" and insert -- Alfa --, therefor.

In the Claims

Column 13
Claim 14, delete "1" and insert -- 10 --, therefor.

Signed and Sealed this
Twenty-fourth Day of October, 2017

Joseph Matal

Joseph Matal
*Performing the Functions and Duties of the*
*Under Secretary of Commerce for Intellectual Property and*
*Director of the United States Patent and Trademark Office*